United States Patent
Valvik et al.

(10) Patent No.: US 10,430,640 B2
(45) Date of Patent: *Oct. 1, 2019

(54) SYSTEM AND METHOD FOR CLASSIFICATION OF PARTICLES IN A FLUID SAMPLE

(71) Applicant: KONINKLIJKE PHILIPS N.V., Eindhoven (NL)

(72) Inventors: Martin Christian Valvik, Hillerod (DK); Niels Agersnap Larsen, Niva (DK); Tommy Winther Berg, Kopenhagen (DK)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/231,650

(22) Filed: Dec. 24, 2018

(65) Prior Publication Data

US 2019/0130162 A1    May 2, 2019

Related U.S. Application Data

(63) Continuation of application No. 15/886,925, filed on Feb. 2, 2018, now Pat. No. 10,192,100, which is a
(Continued)

(30) Foreign Application Priority Data

Dec. 19, 2012 (DK) ................. 2012 70800

(51) Int. Cl.
*G06K 9/00* (2006.01)
*G06T 7/00* (2017.01)
(Continued)

(52) U.S. Cl.
CPC ..... *G06K 9/00147* (2013.01); *G01N 15/0227* (2013.01); *G01N 15/1434* (2013.01);
(Continued)

(58) Field of Classification Search
None
See application file for complete search history.

(56) References Cited

U.S. PATENT DOCUMENTS 5,715,182 A    2/1998  Asai
6,246,785 B1   6/2001  Molnar
(Continued)

FOREIGN PATENT DOCUMENTS

EP    0336608 A2    10/1989
EP    2031428 B1    10/2010
(Continued)

OTHER PUBLICATIONS

Pierre Tibayrenc et al, "Determination of Yeast Viability During a Stress-Model Alcoholic Fermentation Using Reagent-Free Microscopy Image Analysis", AIChE, DOI 10.1002/btpr 549, Published online Feb. 2, 2011 in Wiley Online Library (wileyonlinelibrary.com), pp. 539-546.
(Continued)

*Primary Examiner* — Atiba O Fitzpatrick
(74) *Attorney, Agent, or Firm* — Sherry Austin (57) ABSTRACT

A particle classifier system and a method of training the system are described. The particle classifier system is suitable for classification of particles in a liquid sample, said particle classifier system comprises
an optical detection assembly comprising at least one image acquisition device with an optical axis, the image acquisition device is configured to acquire images of an image acquisition area perpendicular to said optical axis;
(Continued)

a sample device comprising at least one sample container suitable for holding a sample in liquid form;

a translating arrangement configured to translate said image acquisition area through at least a part of said sample container;

a control system configured to controlling said optical detection assembly and said translating unit to acquire images of a plurality of image acquisition areas;

an image analyzing processing system programmed to analyze said acquired images by a method comprising creating objects (sub-images) of individual particles captured by said acquired images, creating stacks of objects of each individual particle, identifying complete stacks of objects comprising at least one object wherein said particle is in-focus, and two objects wherein said particle is out-of-focus, and determining, for each of said complete stacks of objects, a set of values for a set of features of at least N features, wherein N is larger than or equal to 1, and wherein the determination of said values of said set of features involve data obtained from said at least one object wherein said particle is in-focus, and/or said at least two objects wherein said particle is out-of-focus; and an artificial intelligent processing system programmed to associate said set of values for said determined set of features for each individual particle to a particle classification.

15 Claims, 4 Drawing Sheets

Related U.S. Application Data continuation of application No. 14/654,347, filed as application No. PCT/DK2013/050445 on Dec. 19, 2013, now Pat. No. 9,904,842.

(60) Provisional application No. 61/739,323, filed on Dec. 19, 2012.

(51) Int. Cl.
  H04N 13/296 (2018.01)
  G06T 5/50 (2006.01)
  G01N 15/02 (2006.01)
  G01N 15/14 (2006.01)

(52) U.S. Cl.
  CPC ....... *G06K 9/0014* (2013.01); *G06K 9/00127* (2013.01); *G06T 5/50* (2013.01); *G06T 7/0012* (2013.01); *H04N 13/296* (2018.05); *G01N 15/1475* (2013.01); *G01N 2015/144* (2013.01); *G01N 2015/1445* (2013.01); *G01N 2015/1488* (2013.01); *G06T 2207/10056* (2013.01); *G06T 2207/20084* (2013.01)

(56) References Cited

U.S. PATENT DOCUMENTS

| | | | |
|---|---|---|---|
| 6,330,350 | B1 | 12/2001 | Ahn |
| 7,469,056 | B2 | 12/2008 | Ramm |
| 2002/0165837 | A1 | 11/2002 | Zhang |
| 2009/0016785 | A1 | 7/2009 | Bruno |
| 2009/0295963 | A1 | 12/2009 | Bamford |
| 2011/0261164 | A1* | 10/2011 | Olesen ............... G01N 15/1475 348/46 |

FOREIGN PATENT DOCUMENTS

| | | |
|---|---|---|
| WO | 2001082216 A1 | 1/2001 |
| WO | 2006055413 A2 | 5/2006 |
| WO | 2009091318 A1 | 7/2009 |
| WO | 2010063293 A1 | 6/2010 |
| WO | 2010139697 A1 | 12/2010 |
| WO | 2011088091 A1 | 7/2011 |

OTHER PUBLICATIONS

A. Verikas et al, "Phase congruency-based detection of circular objects applied to analysis of phytoplankton images", Pattern Recognition, 45, (2012), pp. 1659-1670, www.elsevier.com/locate/pr.

Huang, Kai et al "Boosting Accuracy of Automated Classification of Fluorescence icroscope Images for Location Proteomics", BMC Bioinformatics, 2004.

* cited by examiner

SYSTEM AND METHOD FOR CLASSIFICATION OF PARTICLES IN A FLUID SAMPLE

CROSS-REFERENCE TO PRIOR APPLICATIONS

This application is a continuation of application Ser. No. 15/886,925, filed on Feb. 2, 2018, which is a continuation of application Ser. No. 14/654,347, filed on Jun. 19, 2015, which is the U.S. National Phase application under 35 U.S.C. § 371 of International Application No. PCT/DK2013/050445, filed on Dec. 19, 2013, which claims the benefit of U.S. Provisional Patent Application No. 61/739,323, filed on Dec. 19, 2012 and Denmark Patent Application No. PA 2012 70800, filed on Dec. 19, 2012. These applications are hereby incorporated by reference herein.

TECHNICAL FIELD

The present invention relates to a particle classifier system suitable for classification of particles in a liquid sample, a method for training a particle classifier system comprising an artificial intelligent processing system, a method of analyzing a test liquid sample for the presence of a target particle and a method of classification of particles in a liquid sample. The particle classifier system and the methods may be utilized in automatic classification of particles in fluids, such as water, blood, urine, milk and similar fluids.

PRIOR ART

In US application no. 0249082 from 2006 Holmertz et al. discloses a method and apparatus for counting somatic cells and fat droplets in milk. The apparatus acquires images of raw milk flowing past the camera in a tube. The images comprise particles of fat droplets, somatic cells and other parts of the milk. The particles are imaged in focus with a high spatial resolution, and after acquisition of the images, they are processed digitally—preferably by using a neural network. The output from the apparatus is a fat droplet count or somatic cell count, from which the concentration is calculated using estimated values for the size of the measuring chamber. The apparatus requires a large number of images (thousands) to get a sufficiently high accuracy of the concentration.

In U.S. Pat. No. 5,715,182 from 1998 Asai et al. discloses a device for classification and examination of particles in fluid. In the presented device a fluid such as urine flows down in a flow cell past a camera, wherein the camera acquires images of the urine in focus. Only one particle is imaged at a time, and after acquisition, a unit extracts characteristics of the particle imaged in focus. Then the characteristics are fed to a neural network trained to differentiate between the particles in question.

In the mentioned prior art classification devices, the particles in the fluid must pass the camera one at a time. This is very time consuming as many images must be acquired for a reasonably good statistic of the resulting classification. Further, only one image (in focus) is acquired of each particle, but as several different particles may look quite equal, it may be difficult to classify them precisely.

U.S. Pat. No. 7,469,056 from 2008 Ramm et al. discloses a system for performing automated cell screening in drug discovery, including an automated microscope, a fast autofocus device and a digital imaging system. Processes are implemented in software through which relevant cellular material is segmented and quantified with minimal user interaction.

WO 2009/091318 by Lindberg et al. discloses a method and apparatus for analysis of particles in a liquid sample. The apparatus disclosed is suitable for acquiring a number of images from a liquid sample comprising particles. The method disclosed comprises identifying images of particles in best focus and using the image in best focus for the particle for identifying the type of particle.

SUMMARY OF THE INVENTION

It is an object of the present invention to provide a particle classifier system suitably for classification of particles in a liquid sample and a method of classification of particles in a liquid sample which is simple and reliable, and where the particle classifier system can be trained in a fast and simple way.

It is further an object of the invention to provide a method for training a particle classifier system comprising an artificial intelligent processing system which method is relatively fast and simple.

It is further an object to provide a method of analyzing a test liquid sample for the presence of a target particle, which method is reliable and fast.

These and other objects have been solved by the invention as defined in the claims and as described herein below.

It has been found that the invention and embodiments thereof have a number of additional advantages which will be clear to the skilled person from the following description.

The particle classifier system suitably for classification of particles in a liquid sample according to the invention comprises an optical detection assembly comprising at least one image acquisition device with an optical axis, the image acquisition device is configured to acquire images of an image acquisition area perpendicular to the optical axis;

a sample device comprising at least one sample container suitable for holding a sample in liquid form;

a translating arrangement configured to translate the image acquisition area through at least a part of the sample container;

a control system configured to controlling the optical detection assembly and the translating unit to acquire images of a plurality of image acquisition areas;

an image analyzing processing system programmed to analyze the acquired images by a method comprising
creating objects (sub-images) of individual particles captured by the acquired images,
creating stacks of objects of each individual particle,
identifying complete stacks of objects comprising
at least one object wherein the particle is in-focus, and
two object wherein the particle is out-of-focus, and
determining, for each of the complete stacks of objects, a set of values for a set of features of at least N features, wherein N is at least 1, and wherein the determination of the values of the set of features involve data obtained from the at least one object wherein the particle is in-focus, and/or the at least two objects wherein the particle is out-of-focus; and an artificial intelligent processing system programmed to associate the set of values for the determined set of features for each individual particle to a particle classification.

The terms 'liquid sample' and 'fluid sample' are used interchangeable.

A 'sub-image' is a segment of an acquired image whereas the term 'object' is used to denote a sub-image which has been selected for further use. Advantageously an object is a sub-image comprising an image of one single particle, preferably the object has passed a pre-test that it comprises an image of one single particle.

In an embodiment, for improved result a sub-image is approved to be an object when it comprises an image of one single particle.

In an embodiment one or more objects are provided by objects with error(s) in form sub-images having errors such as where a part of the object is blurred, where the particle is not fully shown and/or where several particles are clumping. Such one or more objects with errors are preferably only used where a sufficient number of approved objects of one single particle is/are not available.

A 'stack' of objects is a collection of objects of the same particle. A stack usually comprises one object in-focus and a number of objects out-of-focus.

In an embodiment the stack of object comprises a plurality of approved objects of one single particle. Advantageously all objects of the stack is in form of approved objects of one single particle. However in an embodiment the stack of object comprises a plurality of approved objects of one single particle and one or more objects with errors.

A 'feature' is a property for a stack, such as a size, a circumference, a color, etc. A feature value is the determined e.g. calculated value for a given feature, and is advantageously in form of a number (such as 17, 9, or 0.23). In an embodiment the value of a feature is in form of a code—e.g. a color code. All features are to be determined from images acquired of a particle and advantageously determined from objects. Feature extraction and/or feature value determination is advantageously obtained by data-mining.

In an embodiment a number of feature types, such as size or shape are preselected. The optical detection assembly, the sample device, the translating arrangement and the control system may individually or in combination be as they are known from prior art, e.g. as described in WO 2010/063293, US 2011/0261164, EP 2031 428 and US 2009/0295963. These elements are well known in the art. The requirements of these components in combination are that they are capable of holding a liquid sample and are configured to acquire images of a plurality of image acquisition areas within a fixated liquid sample. Preferred examples are described below.

In an embodiment the image acquisition device is a scanning camera configured to scan through at least a part of a liquid in the sample container, the image acquisition device preferably being configured to scan through at least a part of a liquid in the sample container in a scanning direction different from the optical axis.

The sample device advantageously comprises a plurality of identical or different sample containers.

The translating arrangement is advantageously configured to translate the image acquisition area with a step length between each acquired image. The step length is preferably a pre-selected step length. The step length is utilized when determining the distance between objects in the stacks of objects.

In an embodiment the translating arrangement is configured to move the sample device and the optical detection assembly relative to each other, thereby translating the image acquisition area through at least a part of the sample container.

The image analyzing processing system is programmed to analyze the acquired images. The image analyzing processing system (also referred to as the analyzing device) advantageously comprises a memory onto which the acquired images are stored. Advantageously also data regarding the position of the acquired images are stored such that data regarding the position of objects and optionally other sub-images can be retrieved to be stored with the objects e.g. together with the position of the sub-image in the original image (i.e. the acquired image). The size and other relevant data may for example be stored as Meta data in the sub-image.

The objects of individual particles captured by the acquired images are obtained by identifying an image area which appears to comprise only one particle. The segmentation advantageously comprises a process of partitioning a digital image into multiple segments (sets of pixels, also known as super pixels). The goal of segmentation is to simplify and/or change the representation of an image into something that is more meaningful and easier to analyze. Image segmentation is typically used to locate objects and boundaries (lines, curves, etc.) in images. In an embodiment the image segmentation comprising the process of assigning a label to every pixel in an image such that pixels with the same label share certain visual characteristics.

Advantageously the acquired image is first scanned for bad regions such as regions with a poor light level, regions where an item outside the sample container may have obscured the image, regions with signs of flow during the image acquisition, etc. These regions are then discarded from the rest of the procedure. Subsequently a segmentation of the particles in the rest of the acquired image is performed.

The segmentation advantageously comprises identification of each segment in the image that may appear to be an image of a particle. Preferably each identified segment is copied from the rest of the image and this sub-image is advantageously applied to a number of filters, such as a shape-filter, a size-filter, a contrast-filter, intensity filter, etc.

When a sub-image is accepted to comprise an image of a particle (in or out of focus), it is called an "object". When all possible objects in the original image has been identified and logged, the original image may be stored for later use.

In an embodiment the sub-image is accepted to comprise an image of a particle if the sub-image passes one or more filters and the sub-image is then candidate to comprise an image of a particle, and the sub-image is therefore logged and stored. When a sub-image is accepted, it is promoted to be an object.

The creating of stacks of objects of each individual particle is provided by using the data relating to the position of the objects in the liquid sample relative to positions of other objects. Thereby it can be determined which objects shows the same particles in or out of focus.

Each of the objects is added to one of a number of stacks where each stack comprises objects of the same particle. Advantageously each stack comprises information regarding the position where it was found in the liquid sample and/or the respective objects comprises information regarding the position where it was found in the acquired image. Using the position information further objects may be connected to a previously created stack comprising objects of the same particle. If the object cannot be related to a previously created stack, a new stack is advantageously created.

In an embodiment blind segmentation is utilized. In blind segmentation, a new stack is created when an object is found wherein a particle is imaged in focus. Further sub-images are added to the stack by calculating the position in previous and subsequent acquired images and cut-out sub-images of similar size at these positions. In this way there is no guarantee that the sub-images comprises an image of a particle, but the probability is high and for some particle types—in particular relatively large particles—and/or for some particle classifier systems—in particular where the distance between acquired images is relatively low—this procedure works well. Such sub-images found by blind segmentation are referred to a "blind objects". The number of blind objects in a stack may be e.g. 3 or more, 5 or more or even 7 or more. The blind objects are considered to be objects and are treated as such in the image analyzing processing.

A stack may comprise as many objects as desired. Where the translating arrangement comprises a step motor or similar step-wise translating arrangement, the number of objects of a stack will depend on the step-size. Naturally also the size of the particle is relevant for the number of objects in an object stack. Furthermore the depth-of-focus is relevant. In an embodiment each stack comprises from 3 to 100 objects. Advantageously each stack comprises from 5 to 50 objects.

In an embodiment, the image analyzing processing system is programmed to analyze the acquired images by a method comprising creating sub-images (objects) of individual particles captured by the acquired images, wherein each object is created by copying all pixels within a sub-image periphery line surrounding the individual particle and subjecting the copied pixels to a filtration in at least one filter preferably comprising a shape-filter, a size-filter, a contrast-filter or an intensity filter.

The object periphery line surrounding the individual particle may in principle have any shape. In an embodiment the object periphery line surrounding the individual particle is preferably rectangular quadratic, circular, or shaped as a polygon.

In an embodiment, the analyzing processing system is programmed to analyze the acquired images by a method comprising creating objects (sub-images) of individual particles captured by the acquired images and providing stacks of the objects of the individual particles, wherein the objects comprises only one particle each.

In an embodiment, the image analyzing processing system is programmed to analyze the acquired images by a method comprising creating objects of individual particles captured by the acquired images and providing stacks of the objects of the individual particles, wherein the objects comprises a particle free area surrounding the particle. Preferably the particle free area is detectable by the image analyzing processing system.

In an embodiment, the image analyzing processing system is programmed to identify complete stacks of objects, wherein the complete stacks of objects comprises at least one out-of focus object acquired on either side on the in-focus object. This provides an increased reliability of the system.

In an embodiment, the image analyzing processing system is programmed to identify complete stacks of objects, wherein the complete stacks of objects comprises at least 5 objects, such as at least 9 objects, such as at least 15 objects, such as at least 25 objects, such as at least 49 objects, In an embodiment, the image analyzing processing system is programmed to determine values for a predetermined set of features of at least N features for each of the complete stacks of objects, wherein N is 3 or more, such as 4 or more, such as up to about 1000.

Some particles are transparent for optical microscopy when imaged in focus, but may be partly opaque when imaged out of focus. These particles will therefore be detected as objects in the out of focus positions, but will leave a "hole" in the stack when in focus. An "artificial" object from the image may advantageously be applied for an in-focus object.

When no further objects are added to a stack, the stack is to be closed and it is evaluated if the stack is complete in that it is determined if the stack comprises at least one object of the particle in-focus, and at least two images of the particle out-of-focus.

For each object in a stack a focus figure of merit or focus value is advantageously calculated. The focus value is a quantification of how close an object is to be imaged in focus. The higher the focus value, the closer the object is to be in best focus. The focus values for a stack may be plotted. In an embodiment the focus values for a stack is used in the classification in that feature values from stacks with a higher focus value are weighted higher than feature values from stacks with lower focus value.

Advantageously, there is at least one object on each side of the object of the particle in focus. If the stack is complete the stack is considered to be accepted and get the status of being processed. Otherwise the stack of objects is discarded.

When a stack has been processed, it is ready for feature extraction. A large number of features may be defined and calculated and for each of the complete stacks of objects, a set of values for a set of features of at least N features are determined, wherein N is at least 1, and wherein the determination of the values of the set of features involve data obtained from the at least one object wherein the particle is in-focus, and/or the at least two objects wherein the particle is out-of-focus.

The obtained set of values is processed in the artificial intelligent processing system programmed to associate the set of values for the determined set of features for each individual particle to a particle classification.

The artificial intelligent processing system is in an embodiment integrated with the image analyzing processing system and optionally share memory.

In an embodiment the artificial intelligent processing system and the image analyzing processing system are separate elements arranged to be in digital connection e.g. wireless and/or via the Internet.

In an embodiment the particle classifier system comprises two operating modes comprising a training mode and a classification mode. In order to using the particle classifier system for classifying, the particle classifier system should be trained as described in further detail below. Due to the stacking of the objects and the generation of the sets of values for the stack, it has been found that the particle classifier system is relatively simple and fast to train. By a few training processes the particle classifier system will be capable of classifying selected particle types. Further the particle classifier system can be trained using a very simple method which may be performed by users after having received few instructions.

In an embodiment the particle classifier system in its training mode is programmed to associate the values of the set of features with a classification provided by a user of the particle classifier system.

Each set of features associated with a classification is advantageously stored in a memory.

In an embodiment the particle classifier system in its classification mode is programmed to classify a particle based on a set of features from objects of the particle and using the artificial intelligent processing system comprising a plurality of sets of features associated with respective classification stored on the memory.

The artificial intelligent processing system may be any artificial intelligent processing system suitably for classifying the particles. The artificial intelligent processing system advantageously is programmed to have a classification algorithm. In an embodiment the artificial intelligent processing system is programmed to apply a statistic balancing algorithm. Thereby the artificial intelligent processing system is capable of classifying a particle using both exact matches with a learned value set as well as statistical variations thereof.

Advantageously the artificial intelligent processing system comprises a neural network, such as a feed forward artificial neural network comprising a plurality of layers of nodes. According to the invention the image analyzing processing system is programmed to for each of a complete stack of objects, determining a set of values for a set of features of at least N features. The image analyzing processing system of the particle classifier system advantageously is programmed to determine sets of values for a large number of features, which—dependent on the type of particles to be classified—can be selected or deselected.

The features may be any features which alone or in combination with other features can be used to distinguish one type of particles from another type of particles.

Many different features may be defined and implemented. Each of the many features may be determined e.g. calculated for every object stack, but usually a sub-set of features is selected. The features in the sub-set should be selected to provide as much information regarding the difference between the different kinds of particles as possible.

One feature may be the circumference of the object. This feature should advantageously be selected if the particles have different sizes as it will provide useful information regarding the type of particle, but if the particles are of approximately the same size this feature should not be selected or be applied alone When characterizing particles comprised in a fluid such as urine, where one would look for e.g. bacteria, crystals and white blood-cells, one set of features may be optimal, but the same set of features may not provide sufficiently information when the fluid is milk. In milk a different subset may be used for characterizing particles such as fat droplets and somatic cells (in case of mastitis).

In an embodiment the classifier system is suitably for classification of particles of biological or non-biological origin or a combination thereof. The biological particles may be selected from the group of bacteria, archaea, yeast, fungi, pollen, viruses, blood cells, such as leukocytes, erythrocytes, and thrombocytes; oocytes, sperm, zygote, stem cells, somatic cells, crystals, fat droplets and mixtures thereof.

The features may comprise features based on a thresholded object in focus, such as:
    spatial descriptors such as area, length of perimeter, area of enclosing circle etc. and/or
    morphological descriptors such as convexity, eccentricity, shape factor etc. and/or
    binary moments The features may also comprise features based on a grayscale version of an object in focus, such as
    contrast, light scattering properties, absorption etc. and/or
    various types of grayscale moments and/or
    features extracted in the Fourier space of the focused grayscale image, and/or
    Granularity The features may also comprise features based on a color version of an object in Focus, for example
    pre-dominant color pattern and/or
    hue.

Further the features may comprise features based on information from the object stack (i.e. a number of objects in and out of focus), such as
    signatures/descriptors of various focus curves of the object, such as FWHM, AUC, variance between the curve and a smoothed curve etc. and/or
    signatures/descriptors of various intensity curves of the object, such as FWHM, AUC, variance between the curve and a smoothed curve etc. and/or
    signatures/descriptors of curves generated by applying grayscale/binary features to individual objects in the object stack,
    assessment of temporal parameters of the stack,
    phase and absorption map, Brownian movement and self-propelled characteristic, and/or
    flow characteristic.

In an embodiment the image analyzing processing system is programmed to determining values for a set of features comprising at least one of
    features relating to out-of-focus objects,
    features relating to grayscale versions of in-focus objects,
    features relating to color versions of in-focus objects,
        features relating to thresholded versions of in-focus objects and/or
    features relating to both in-focus and out-of-focus objects In an embodiment the features relating to out-of-focus objects may comprise one of
    circumference of the particle (shape),
    size of particle (cross-sectional area),
    ratio between the largest and the smallest diameter,
    color variation (degree of color variation) and/or
    pre-dominant color pattern.

In an embodiment the features relating to in-focus objects comprises at least one of
    circumference of the particle (shape),
    size of particle (cross-sectional area),
    ratio between the largest and the smallest diameter,
    color variation (degree of color variation),
    predominant color pattern, and/or
    number of sub-particles inside the circumference of the particle.

In an embodiment the features relating to both out-of-focus objects and in-focus objects comprises at least one of
    difference(s) in circumference of the particle (shape) from one object to another,
    difference(s) in size of particle (cross-sectional area) from one object to another,
    difference(s) in ratio between the largest and the smallest diameter from one object to another,
    difference(s) in color variation (degree of color variation) from one object to another,
    difference(s) in predominant color pattern from one object to another,
    difference(s) in color from one object to another and/or
    distance between respective object.

When a selected set of features has been determined for an object stack, the feature values are passed to the next step in the procedure—the final classification. In an embodiment a feature set is advantageously a list of values such as (17, 3, 199, . . . , 0.11), where each value is a determined e.g. calculated value for a specific feature. In an embodiment the feature set is in form of a binary pattern.

In an embodiment the selection of features is simplified by using different kinds of scatter plots in two or more dimensions.

In an embodiment the selection of features comprises data mining to find significant features—such as features that differ significantly from one particle type to another.

Advantageously the artificial intelligent processing system is capable of associating a set of features with a specific class of particles, the set of features is obtained from a complete stack of objects of a particle and the associating of the a set of features with the specific class of particles is based on a statistic balancing and processing of a plurality of sets of features associated with the class of particles and a plurality of sets of features associated with at least one other class of particles.

In an embodiment the values for each feature in a set of features are calculated for each stack, but the particles remain unclassified. Then the sets of features are combined into an ensemble of features. This ensemble covers all particles in the fluid sample, and to this ensemble a set of features may be assigned and determined. An example of an ensemble feature may be the average size of the particles, but could be any feature determined for the stacks. Further, the features for the ensemble comprise features related to the shape or density of a plot of the features. The set of features for the ensemble may be utilized as information for classifying each individual particle relative to the ensemble. The result is a set of particle features, which are defined relative to the ensemble.

In an embodiment the particle classifier system is adapted to sequentially acquire sets of images and classify particles captured by a first set of images and particles captured by at least a second set of images, creating a first ensemble of stacks of objects from the first set of images and a second ensemble of stacks of objects from the second set of images.

The number of sets of images may be as high as desired. Advantageously the respective sets of images are obtained by respectively scanning's through the sample or a part of the sample where a time delay is provided between the respective scanning's. Thereby changes of the respective particles can be observed. This embodiment is very suitably for analyzing of biological particles e.g. living particles. In that way growth can be analyzed. This method may also be applied for analyzing decay of particles. The time delay between the respective scanning's can be selected in dependence on the expected rate of the changes which are likely to occur.

An ensample of stacks comprises at least one stack and advantageously a plurality of stacks. In an embodiment the system is adapted to identify stacks of objects of the first ensemble of individual particles and stacks of objects of the second ensemble of the respective individual particles and detect changes between the stacks of objects of the first ensemble and stacks of objects of the second ensemble of the respective individual particles. The detection of changes can advantageously be performed immediately after a scanning and the time delay to a subsequent scanning can be regulated to provide a desired degree of changes. Thereby the development time of one or more particles can be determined.

In an embodiment the system is adapted to determine Brownian movement of a particle from objects in a stack.

Advantageously a set of features of at least N features is determined for stacks of objects of the ensembles where the N features can be as described above.

In an embodiment the particles are reclassified using features from the ensembles of stacks of objects. For example the stacks of objects of the first ensemble of individual particles may result in a first classification and the stacks of objects of a second or a further ensemble of individual particles can result in a reclassification e.g. a finer classification because further data is obtained.

In an embodiment the image analyzing processing system is adapted to determine values for a set of features for each stack of objects of particles that have not yet been classified (unclassified particles), and to create an ensemble of sets of features, and wherein the image analyzing processing system is adapted to classify these previously unclassified particles using the ensemble of sets of features.

When training a particle classifier system there are several procedures that may be followed. One approach is to feed the particle classifier system with a liquid sample comprising only one type of particle. The particles are then classified to the same class, and a set of features may be selected that best describes the particle.

This may be done several times using different types of particles in the sample, and for several samples comprising the same type of particles. In this way a library of stacks may be created where every type of particle is represented by many stacks of objects.

The optimum set of features for one type of particle may not be the optimum set for another type of particle. When two or more different types of particles are present in one liquid sample, a combined set of features may be selected among all the sets of features that give the best possible classification of the particles.

The invention therefore also relates to a method for training a particle classifier system. The method comprises using an artificial intelligent processing system for classifying of at least one individual particle in a liquid sample, the method comprises providing one or more liquid samples comprising together at least one first type of particle and at least one second type of particle, acquiring at least 3 images of a plurality of the first type of particle and a plurality of the second type of particle in the liquid sample, wherein the individual first type and second type of particles respectively are in-focus or out-of-focus, creating objects (sub-images) of the individual particles captured by the acquired images and providing stacks of objects for each first type of particle and for each second type of particle and identifying complete stacks of objects comprising at least one object wherein the particle is in-focus, and two objects wherein the particle is out-of-focus, determining a set of features of at least N features for each of stacks of objects, wherein N is larger than 0, and wherein the determination of the features involve data obtained from the at least one object wherein the particle is in-focus, and the at least two objects wherein the particle is out-of-focus, and training the artificial intelligent processing system by feeding it with data comprising first type sets of data associated with a first type of a particle class and second type sets of data associated with a second type of a particle class.

The method for training may utilize a particle classifier system similar to the system described earlier for classifying particles.

In an embodiment, the method comprises providing a liquid sample comprising a plurality of a first type of particles and a plurality of a second type of particles and training the artificial intelligent processing system using the sets of data obtained from the particles in the provided liquid samples. This may be done for several liquids samples preferably with different concentrations of the first type and the second type of particles.

A simpler approach is to use a training method where only one type of particle is present in the liquid sample. This is preferably done using several different liquid samples of the same particles, i.e. the method comprises providing at least one liquid sample comprising exclusively one type of particle and training the artificial intelligent processing system using sets of data obtained from the particles in the provided liquid sample(s).

In some cases it may be very difficult or impossible to obtain a liquid sample comprising only one type of sample. In these situations it is sufficient to know that a certain percentage of the particles are of one type only.

The rest of the particles may be of several different types. During training the classifier system is advantageously provided with the information that a percentage e.g. 75% of the particles are of one type, and the rest of the particles are of one or more different types. The classifier system may then be adjusted so as the output equals this wanted result.

In an embodiment the method for training comprises providing at least one liquid sample comprising a predominantly amount of one type of particles, preferably at least about 75% of the particles, such as at least about 80% of the particles, such as at least about 85% of the particles, such as at least about 90% of the particles, such as at least about 95% of the particles are the same type of particle; and training the artificial intelligent processing system using sets of data obtained from the particles in the provided liquid sample(s).

In an embodiment the method comprises providing at least one liquid sample comprising only a first type of particles and providing at least one liquid sample comprising only a second type of particles and training the artificial intelligent processing system using sets of data obtained from the particles in the provided liquid samples.

In an embodiment the method for training the classifier system comprises using supervised learning or a semi-supervised learning.

In supervised learning a skilled person classifies a number of particles and feed the results to the classifier system. When a preferable large number of particles has been manually classified and feed to the classifier system, a set of features may be selected so as to let the classifier system give the same results as obtained manually. When utilizing a semi-supervised learning system, a skilled person classifies a number of particles and feed the results to the classifier system. The classifying system will continuously learn and get better in making a correct classification of new particles. For new particles the classifying system proposes a classification and the skilled person accepts or rejects the proposed classification. In case of a rejection, the skilled person may correct the classification and thereby providing more "knowledge" or experience to the classifying system.

In an embodiment the method for training a classifier system comprises providing one or more liquid samples comprising together T different types of particles where T is 3 or more, providing complete stacks for the particles, determining features from the stacks and training the artificial intelligent processing system using the sets of features associated with the respective type of particle class.

In some situations a screening of a fluid sample for specific types of particles is needed. In these cases the fluid sample may be considered to comprise particles of a target type and particles of no specific interest.

In an embodiment the method for training a classifier system a first type particles are of a target type and a second type particles are not of the target type.

In an embodiment of the method for training a classifier system the target type is particles selected from the group of bacteria, archaea, yeast, fungi, pollen, viruses, leukocytes, such as granulocytes, monocytes, Erythrocytes, Thrombocytes, oocytes, sperm, zygote, stem cells, somatic cells, crystals, fat droplets and mixtures thereof.

When a system has been trained with fluid samples comprising a set of target particles, the system may be utilized for screening a test fluid for the presence of one or more of the target particles.

The artificial intelligent processing system is advantageously performing the processing using a classification algorithm. The input to the classification algorithm comprises the values for the sub-set of features, and the output is the type of particle (or a code for such particle), such as bacteria, fat droplet, white blood cell, red blood cell, crystal, etc. etc. In an embodiment a counter has been assigned to each of the expected types of particles, and the counter for the particular identified type of particle is increased by one each time a particle has been identified.

Where the artificial intelligent processing system performing the processing using a classification algorithm it can for example be trained as described above.

In an embodiment when the classification algorithm has been applied on all processed stacks and the particle type determined, a volume of the liquid may be determined. The volume may be determined using information from the number of full images acquired, the step size of the translating arrangement and the discarded parts of the images.

When the volume has been determined, an overall particle concentration may easily be calculated, as well as particle concentrations of each type of particle. Finally it may be decided if the overall number of particles and the different particle concentrations are sufficient for a reliable measurement result, or if acquisition of a new image should be initiated and added to the result. When the total result of the measurement is determined to be sufficiently accurate, the measurement procedure is stopped.

In an embodiment of the method of analyzing a liquid sample the method comprises sequentially acquire sets of images and classify particles captured by a first set of images and particles captured by at least a second set of images, creating a first ensemble of stacks of objects from the first set of images and a second ensemble of stacks of objects from the second set of images preferably as described in the above description of the system. In an embodiment a characterization of the whole sample or a fraction thereof is obtained by determine sets of features of an ensemble of stacks of objects and determine an ensample feature array also referred to as a feature cloud, which can for example provide information at cloud level that cannot be assessed direct from features at particle level, but which can be detected from a plurality of stacks of objects from an ensample.

By this method sets of features of stacks can be used as data points in a feature space, where each point represents a particle, and thereby the feature cloud can be determined.

Examples of characterizations that can be determined by cloud feature(s) are cloud moments, cloud shape parameter, number of clusters, cloud density and etc.

In an embodiment the cloud feature(s) can provide information about temperature, pressure, entropy, etc. due to the general appearance of the particles in the sample.

In an embodiment the method comprising correlating or comparing determined cloud feature(s) to determinations provided on known samples and thereby assessing the state or characteristics of the sample.

Samples populated with identical specimens, e.g. bacteria or yeast, and grown at equal conditions are expected to have same cloud density/distribution in the feature space. This means any cloud feature is expected to be statistical equal.

Any changes of the sample that occur due to internal or external effects are expected to change the cloud density/distribution, and thus alter the corresponding cloud features which in turn can be used to characterize the state of the population in the sample.

Examples of effects that can be detected by use of cloud features e.g. by cloud correlation are
nutrition
environment such as temperature, pH, antibiotics
contamination (A sample is contaminated by a secondary population that evolves to a detectable level over time)
breading (Concentration increases and a secondary effect may be evolving, distribution of sizes)
activity
mutation (may change the shape of the cloud due to appearance of new values of particle feature in the cloud)
structural mode/development (cluster formation, different life cycle of specimens, ageing, live/dead)

The assessment of population state using cloud features e.g. cloud correlation may be divided into characterization of a sample or time evolution of particles in a sample.

In an embodiment a method is utilized for analyzing a test liquid sample for the presence of a target particle using a trained particle classifier system, the particle classifier system being trained to classify the target particle, the method comprising
providing the test liquid sample,
acquiring at least 3 images of individual particles in the liquid sample, wherein the particles respectively are in-focus or out-of-focus,
creating sub-images (objects) of the individual particles captured by the acquired images and providing stacks of objects for each individual particle and identifying complete stacks of objects comprising at least one object wherein the particle is in-focus, and two objects wherein the particle is out-of-focus,
determining a set of features of at least N features for each of the stacks of objects, wherein N is at least 1, and
allowing the artificial intelligent processing system to associate the set of values for the determined set of features for each individual particle to classify the particles and determine if at least one target particle has been classified.

In some situations it is desired to do more than just detecting if a target particle is present in a fluid sample. It may be desirable to know the number of target particles present in a given volume of the fluid sample—i.e. the concentration. It may also be desirable to know the relative concentration compared to other types of particles, because there are more than one kind of target particle. This is the case when using blood for measuring. In an embodiment when determining the so called 3 parts diff or 5 parts diff, the number of each of the different white blood cells (neutrophils, lymphocytes, monocytes, eosinophil's and basophils) is determined, and their relative concentrations are advantageously calculated.

In an embodiment of the method for analyzing a test liquid, the method comprises performing a quantitative analyze determining the number of target particles in the test liquid.

In an embodiment the method for classification of particles in a liquid sample using a trained particle classifier system comprises
acquiring at least 3 images of the individual particle in the liquid sample, wherein the individual particle is in-focus or out-of-focus
creating sub-images (objects) of the individual particle and assigning each of the objects to a stack of objects comprising different images of the individual particle, such that the stack of objects comprises at least one object wherein the particle is in-focus, and two objects wherein the particle is out-of-focus,
determining a set of features of at least N features for the stack of objects, wherein N is larger than 0, and wherein the determination of the set of feature involve data obtained from the at least one object wherein the particle is in-focus, and the at least two objects wherein the particle is out-of-focus,
feeding the set of features to an artificial intelligent processing system of a trained particle classifier system and for classifying the individual particle, and
allowing the artificial intelligent processing system to associate the set of values for the determined set of features for each individual particle to classify the particles.

All features of the inventions including ranges and preferred ranges can be combined in various ways within the scope of the invention, unless there are specific reasons not to combine such features.

BRIEF DESCRIPTION OF THE DRAWINGS

Preferred embodiments of the present invention will now be described, by way of example, with reference to the accompanying drawings. It should be understood that the description of these preferred embodiment should not be interpreted to limit the scope of the invention

The figures are schematic and may be simplified for clarity. Throughout, the same reference numerals are used for identical or corresponding parts.

PREFERRED EMBODIMENTS

The system of the present invention comprises an optical detection assembly. The optical detection assembly comprises in a preferred embodiment at least one image acquisition device comprised of a CCD-camera or a CMOS camera. The optical detection assembly further is comprised of lenses, prisms, irises, apertures and other common optical components used in microscopy. The optical detection assembly is adapted to acquire images wherein individual biological organisms may be identified. One embodiment of an optical detection assembly is described in US provisional application U.S. 61/146,850, wherein an apparatus for obtaining a plurality of images of a sample arranged in relation to a sample device is provided. The apparatus comprises at least a first optical detection assembly comprising at least a first image acquisition device. The first optical detection assembly has an optical axis and an object plane. The object plane comprises an image acquisition area from which electromagnetic waves can be detected as an image by the first image acquisition device. The apparatus further comprises at least one translating arrangement arranged to move the sample device and the first optical detection assembly relative to each other, and a housing arranged to support the first optical detection assembly and the translating arrangement, wherein the first optical detection assembly and the translating arrangement are arranged so that at least a part of the sample device is intersected by the image acquisition area. The movement of the sample device and the first optical detection assembly relative to each other is along a scanning path, which defines an angle theta relative to the optical axis, wherein theta is larger than zero.

U.S. 61/146,850 also discloses a method for obtaining a plurality of images of a sample. This method comprises arranging the sample in relation to a sample device and arranging the sample device in relation to an apparatus for obtaining a plurality of images. The apparatus comprises at least a first optical detection assembly having at least a first image acquisition device. The first optical detection assembly is having an optical axis and an object plane, where the object plane has an image acquisition area from which electromagnetic waves can be detected as an image by the first image acquisition device.

The image acquisition area intersects at least a part of the sample. The sample device and the first detection assembly are moved relative to each other over a scanning length along a first scanning path. The scanning path and the optical axis together define an angle theta, which is larger than zero. The method furthermore comprises obtaining the plurality of images.

In U.S. 61/146,850, is further disclosed a system for obtaining a plurality of images of a sample. The system comprises a sample device and an apparatus having at least a first optical detection assembly comprising at least a first image acquisition device. The first optical detection assembly of the apparatus has an optical axis and an object plane. This object plane comprises an image acquisition area from which electromagnetic waves can be detected as an image by the first image acquisition device. The apparatus of this system further comprises at least one translating arrangement arranged to move the sample device and the first optical detection assembly relative to each other, and a housing arranged to support the first optical detection assembly and the translating arrangement, wherein the first optical detection assembly and the translating arrangement are arranged so that at least a part of the sample device is intersected by the image acquisition area. The movement of the sample device and the first optical detection assembly relative to each other is along a scanning path, which defines an angle theta relative to the optical axis, wherein theta is larger than zero. In principle, the scanning path of U.S. 61/146,850, may comprise any movement of the object plane and the sample relative to each other. In particular, the scanning path may comprise a substantially straight scanning line arranged along a scanning axis. The scanning path may also be defined by a substantially rotational movement, in which case theta is the angle between the optical axis and the local tangential of the rotational movement. In an embodiment, the scanning path is confined to a plane, such as a straight line, a circular movement, a spiral movement, or any other suitable path.

Figure 1:
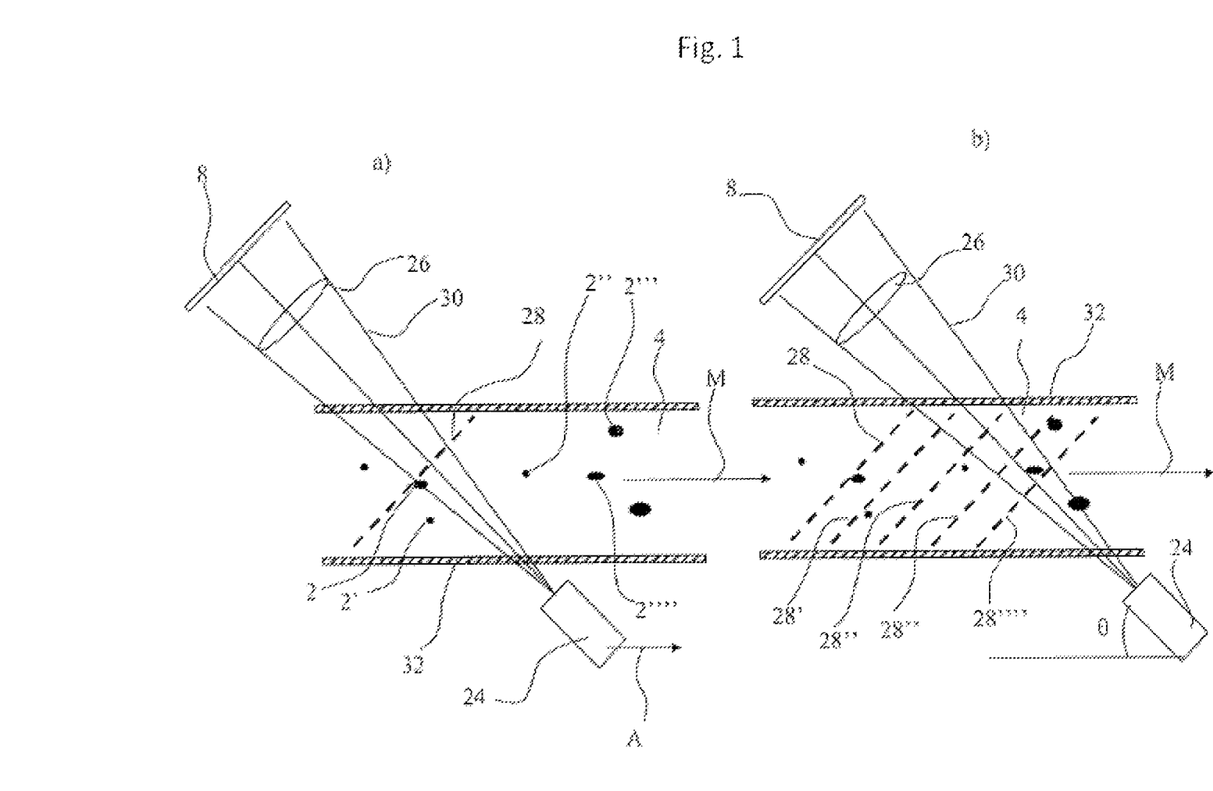
FIG. 1 shows an example of an optical detection assembly and a sample holder comprising a sample of fluid comprising particles.

A preferred embodiment of an optical detection assembly according to the present invention is shown in FIG. 1a, a sample device 32 comprising a fluid sample 4 comprising a pluralities of particles 2, 2', 2", 2''', 2'''' is shown. The sample device 32 has a longitudinal translation axis Z. A light source 24 is provided at one side of the sample holder, and an objective lens 26 and an image sensor 8 is provided on the other side of the sample holder. The light source 24 transmits light 30 through the fluid sample 4 towards the image sensor 8, wherein images of the particles 2, 2', 2", 2''', 2'''' in the fluid sample 4 is acquired when they are in the field of view of the image sensor. A translating arrangement (not shown) may translate the sample device 32 relative to the image sensor 8 in small steps, and for each step a new image is acquired.

In FIG. 1b, the optical detection assembly comprising the image sensor, the lens 26, and the light source 24 has been moved in 4 steps in the scanning direction A. The particles 2, 2', 2", 2''', 2'''' has been imaged by the image sensor in the positions 28, 28', 28", 28''', 28''''. Some of the particles 2, 2', 2", 2''', 2'''' may have been imaged in all 5 positions 28, 28', 28", 28''', 28'''', while some for the particles 2, 2', 2", 2''', 2'''' may only have been imaged in one or two of the images 28, 28', 28", 28''', 28''''. Particles 2, 2', 2", 2''', 2'''' positioned close to the image positions 28, 28', 28", 28''', 28'''' is imaged in focus while particles 2, 2', 2", 2''', 2'''' positioned further away) but still inside the field of view of the image sensor) will be imaged out of focus.

The depth of field of the system, in connection with the step size of the translating arrangement, may be arranged to make sure, that a given particle is imaged in-focus in one image, and imaged out-of-focus in at least one image on each side of the image, wherein the image is in-focus. I.e. if a particle 2" is imaged in-focus in image 28", then it will be imaged out-of-focus in image 28' and 28'''. It may also be imaged out-of-focus in images 28 and 28'''', but the image quality may be too poor to be used. In another example, the particle 2" is imaged in-focus in image 28', 28" and 28''', while the images 28 and 28'''' are out-of-focus.

Figure 2:
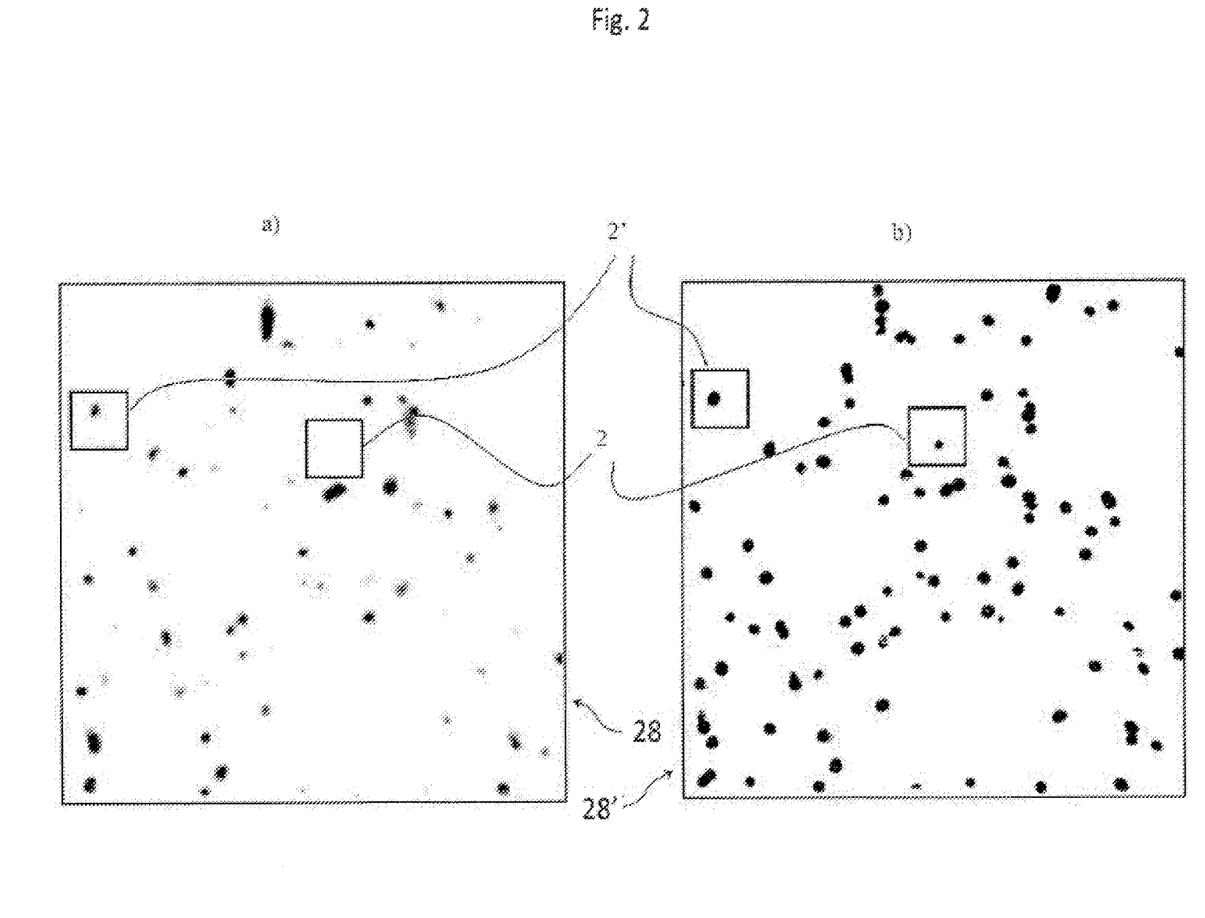
FIG. 2 shows an example of two images of a fluid sample comprising a large number of particles.

In FIG. 2a, an image 28 acquired from a fluid in a sample holder is shown, the fluid comprising a large number of particles. Two particles 2 and 2' has been marked. In FIG. 2b, an image 28' is shown, the image 28' being the next in line when acquiring images. Also in FIG. 2b two particles 2 and 2' has been marked. As may be seen, the particle 2 is imaged in-focus in image 28 and out-of-focus in image 28', while the opposite is the case for the particle marked 2'.

Figure 3:
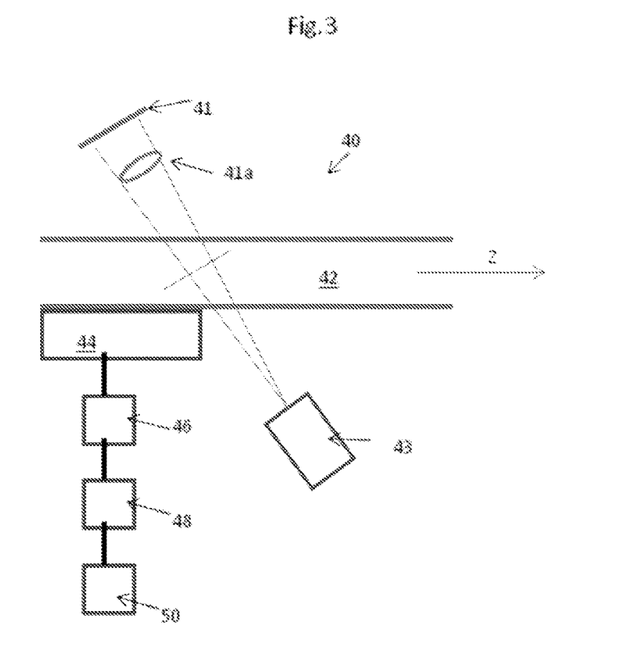
FIG. 3 shows a schematic diagram of the system according to the invention.

In FIG. 3, a schematic of a system according to the present invention is displayed. The system comprises an optical detection assembly 40 comprising an image acquisition device 41 and a lens 41a. The optical detection system may be a standard optical microscope with build-in camera. In FIG. 3 an optical microscope with oblique viewing is shown. An illumination device 43 transmits light, such as laser light or light from a LED through a sample device 42 towards the optical detection assembly 40. The fluid comprising particles to be imaged is contained in the sample device 42. The system comprises a translating arrangement 44. The sample device 42 may be translated along Z-axis relative to the optical detection assembly 40 using the translating arrangement 44, thereby moving particles in the fluid past the image acquisition zone. The step length of the movement is controlled by the translating arrangement 44 so as to make sure that a plurality and advantageously all particles are imaged at least 3 times—one time in-focus and at least two times out-of-focus.

The optimal step length may be determined by the optical system, i.e. the depth of field and the requirements for optical resolution. If the system has a large depth of focus, the step length may be increased, while a low depth of focus may call for small steps. A smaller depth of focus may provide a larger viewing angle, enabling a larger number of particles to be scanned at the same time, but also a poorer optical resolution of the particles imaged.

The system further comprises a control system 46, adapted to control the movement of the translating arrangement 44 relative to the optical detection assembly 40 as well as controlling the image acquisition from the camera. The method for example comprises translating the sample device 42 one step, acquiring an image from the camera, and transferring the image to an image analyzing device 48 of the system. While the image analyzing device 48 is analyzing the image, the control system 46 initiates the translation for a new image to be acquired.

When an image arrives at the analyzing device 48 it is stored in a memory. The image is first scanned for bad regions such as regions with a high/low light level, regions where an object outside the sample container may have obscured the image, etc. These regions are then discarded from the rest of the procedure. Then a segmentation of the particles in the rest of the image is performed. Segmentation comprises identification of each segment in the image that may appear to be an image of a particle. Each identified segment is copied from the rest of the image and this sub-image is applied to a number of filters, such as a shape-filter, a size-filter, a contrast-filter, intensity filter, etc. If the sub-image passes these filters, the sub-image is candidate to comprise an image of a particle, and the sub-image is therefore logged and stored. Data regarding the position of the sub-image in the original image, the size and other relevant data is stored as Meta data in the sub-image. Usually a sub-image is rectangular, but it may in principle be of any shape, as long as the shape is described in the Meta data.

When a sub-image is accepted to comprise an image of a particle (in or out of focus), it is called an "object". When all possible objects in the original image has been identified and logged, the original image may be stored for later use.

Each of the objects is then added to one of a number of stacks of objects. An object stack comprises objects identified in previous images. Each stack comprise information regarding the position where it was found in the image, and using this information new objects may be connected to a previously created object stack comprising objects of the same particle. If the object cannot be related to a previously created stack, a new stack of objects is created.

A stack of objects is open as long as new objects are added to the stack. A stack may comprise many objects depending on the step-size of the translating arrangement and the depth-of-focus. Usually a stack comprises from 1 to 20-25, but it may comprise as many as 45-50 objects or even more. If a new image acquisition does not end up in adding a new object to a particular stack, the stack may be closed. This may happen when the translating arrangement 44 has moved the camera out of range for the particle.

Figure 4:
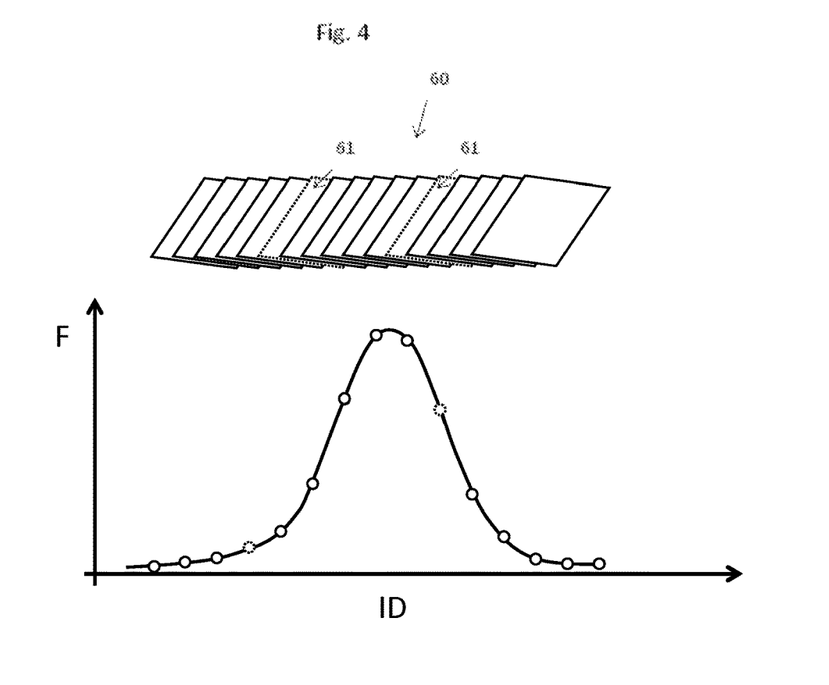
FIG. 4 shows an example of a focus curve calculated for a stack of objects.

For each object in a stack a focus figure of merit or focus value is calculated. The focus value is a quantification of how close an object is to be imaged in focus. The higher the focus value is, the closer the object is in focus. The focus values for a stack of objects 60 may be plotted as shown in FIG. 4 showing focus values as a function of ID, which is the identified order of the objects of the stack. As may be seen, the curve has a top point indicating that the object closest to the top point is the object imaged in focus. The other objects on the curve are imaged more or less out of focus.

The system further comprises an artificial intelligent processing system 50 for classifying of particles. The artificial intelligent processing system is trained as described above. Advantageously the artificial intelligent processing system 50 and the image analyzing processing system are integrated in a common unit.

As may be seen from FIG. 4 two of the focus values F from objects 61 are missing—indicated by a dotted square where they should be expected to be. Sometimes during acquisition of images a region of an image is discarded, and if the discarded region comprises objects belonging to an open object stack, the object will be missing leaving a "hole" in the focus curve. It may therefore be advantageous to leave a stack of objects open even if no new objects are added to the stack.

Some particles are transparent for optical microscopy when imaged in focus, but may be partly opaque when imaged out of focus. These particles will therefore be detected as objects in the out of focus positions, but will leave a "hole" in the stack when in focus. This "hole" may be 1, 2 or even 5 or more positions depending on the step size and the depth of focus.

To fill out the holes in the object stacks it may therefore be advantageous to cut out "artificial" objects from the image and add to a stack for a number of positions until the out of focus objects appears or the object is not discarded due to a bad region. If no new real objects are added to the stack after a number of image acquisitions, the artificial objects may be removed from the stack and the stack may be closed.

When a stack of objects has been closed, the stack is passed on to the next level. In this level it is determined if the stack comprises at least one object of the particle in-focus, and at least two images of the particle that may be out-of-focus. If there is at least one object on each side of the object of the particle in focus, the stack is considered to be accepted and get the status of being processed. Otherwise the stack of objects is discarded.

When a stack has been processed, it is ready for feature extraction. A large number of features may be defined and calculated and only a few will be mentioned here. A skilled person in the art will appreciate that many more different features may be defined and calculated.

The features may advantageously be as described above and preferably comprising features based on a thresholded object in focus, such as:
  Spatial descriptors such as area, length of perimeter, area of enclosing circle etc.
  Morphological descriptors such as convexity, eccentricity, shape factor etc.
  Binary moments The features may also comprise features based on a grayscale version of an object in focus, such as
  Contrast, light scattering properties, absorption etc.
  Various types of grayscale moments
  Features extracted in the Fourier power spectrum of the focused grayscale image Further the features may comprise features based on information from the object stack (i.e. a number of objects in and out of focus), such as Signatures/descriptors of various focus curves of the object, such as FWHM, AUC, variance between the curve and a smoothed curve etc.

Signatures/descriptors of various intensity curves of the object, such as FWHM, AUC, variance between the curve and a smoothed curve etc.

Signatures/descriptors of curves generated by applying grayscale/binary features to individual objects in the object stack.

At present, app. 80 different features have been defined and new features is defined and implemented in the system regularly. Each of the many features may be calculated for every object stack, but usually a sub-set of features is selected. The features in the sub-set should be selected to provide as much information regarding the difference between the different kinds of particles as possible.

One feature may be the circumference of the object. This feature should be selected if the particles have different sizes as it will provide useful information regarding the type of particle, but if the particles are of approximately the same size this feature should not be selected.

When characterizing particles comprised in a fluid such as urine, where one would look for e.g. bacteria, crystals and white blood-cells, one set of features may be optimal, but the same set of features may not provide sufficiently information when the fluid is milk. In milk a different subset may be used for characterizing particles such as fat droplets and somatic cells (in case of mastitis).

When a selected set of features has been calculated for an object stack, the feature values are passed to the next step in the procedure—the final classification. The feature set may be a list of values such as (17, 3, 199, . . . , 11) where each value is a calculated value for a specific feature.

The set of features are transferred to the artificial intelligent processing system 50 for classifying of particles.

Example 1

Example: Viability of Yeast Cells

In this example a method of classifying yeast cells using a particle classifier system as described above is described. The yeast cells are classified as either "dead" or "alive".

A liquid sample comprising a plurality of yeast cells were analyzed using the particle classifier described above and a plurality of stack of objects were obtained, each stack comprising at least one in-focus and two out-of focus objects.

In FIG. 5 the objects of a stack of a yeast cell is shown. In the upper left corner the object is negatively defocused. The objects are aligned in an order of left to right, row after row.

Figure 5A:
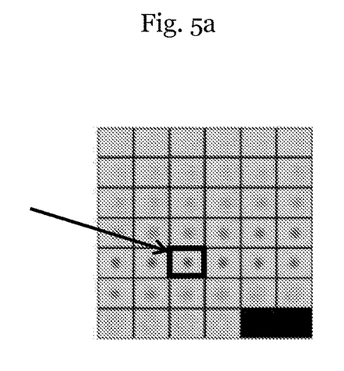
FIGS. 5a, 5b 6a and 6b illustrates objects of two stacks of objects and focus curves for the stacks obtained in example 1.
Figure 5B:
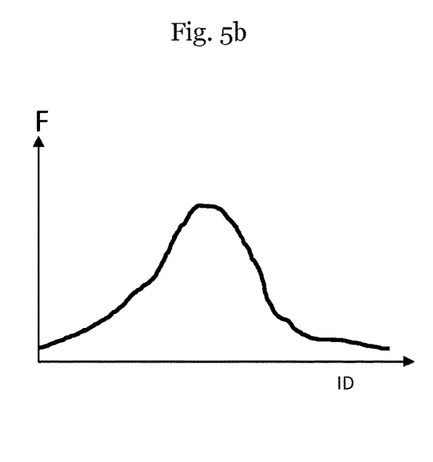

Following the order of the objects it can be seen that the focus F gradually increases and finally arrives at perfect focus (in-focus object), denoted by an arrow and framed with a fat line. The following objects are gradually defocused (positively defocus). In this way the complete focus behavior of a single yeast cell can be viewed in one composite image as shown in FIG. 5a. FIG. 5b shows a focus curve for the stack of FIG. 5a.

Figure 6A:
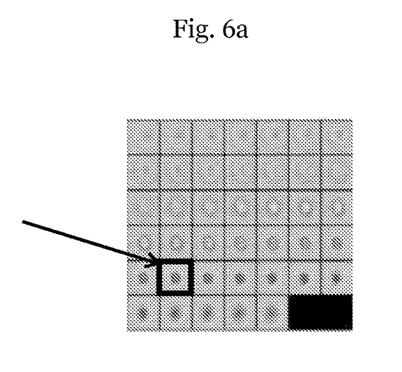
Figure 6B:
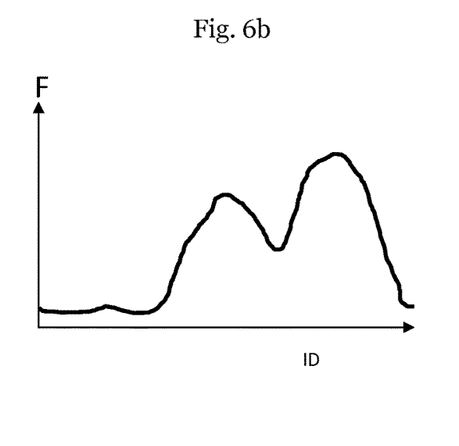

FIG. 6a shows objects of another stack of objects aligned in an order corresponding to the object of the stack of FIG. 5a. FIG. 6b shows a focus curve for the stack of FIG. 6a.

The particle classifier system is classifying the yeast cell viewed in FIG. 5a as a dead yeast cell and the yeast cell of FIG. 6a as a living yeast cell.

If looking only at in-focus objects i.e. as indicated with the arrow there is no distinct difference in the appearance and it is very difficult—and sometimes even impossibly—to judge the viability ("dead" or "alive") of a cell. No morphological or textural features will reveal if the cell is dead or alive.

However, when using out-of-focus information of the yeast cell, it can be seen that it becomes much simpler to judge the viability. For example some of the out-of-focus objects of FIG. 6a shows a bright spot in the center of the living yeast cell. The out-of focus objects of FIG. 5a does not have that feature.

Further it can be seen that the focus curves as shown in FIGS. 5b and 6b differs significantly from each other. For the dead cells the focus curve appears as unimodal Gaussian shaped curve, i.e. it only has a single maximum. For the living cells the focus curve appears as a bimodal Gaussian shaped curve, i.e. with two distinct maxima.

Example 2

Using Ensemble Features to Classify Particles:

In a sample of monoculture yeast cells of unknown size or shape, we want to classify each cell according to the stage of spawning. It is assumed that all cells are in a spawning state where they are either alone (not spawning), two cells connected (spawning with a single offspring), or multiple objects connected (higher level of spawning). After segmentation, stack generation and feature calculation, the size distribution of the particles will show peaks around multiples of a single cell size, i.e. peaks around 1 unit size, 2 unit sizes, etc. It is clear that the area corresponding to the lowest peak corresponds to the size of a single cell, which was unknown up to this point. All particles in the ensemble can now be classified according to the peak in the distribution they are closest to, i.e. particles closest to the lowest peak are not spawning, and particles closer to the second peak are classified as single offspring cells.

What is claimed is:

1. A system for classifying particles in a water sample, system comprising:
    an optical detection assembly comprising at least one image acquisition device and corresponding lens with an optical axis, the image acquisition device is configured to acquire images of an image acquisition area perpendicular to the optical axis;
    a sample device comprising at least one sample container suitable for holding a water sample in liquid form comprising particles;
    a translating arrangement configured to translate said image acquisition area through at least a part of said sample container with a step length between each acquired image;
    a controller configured to control said optical detection assembly and said translating arrangement to acquire images of a plurality of image acquisition areas;
    an image processor programmed to analyze said acquired images and to determine a set of features for an individual particle captured by said acquired images by creating objects of the individual particle and assigning each of the objects to a corresponding stack of objects comprising different images of the individual particle; and
    an artificial intelligent processor programmed to associate said set of features for said individual particle to a particle classification of particles,
    wherein said step length between each acquired image is used to determine a distance between the objects in the stacks of objects.

2. The system as claimed in claim 1 wherein said particle classifier system comprises two operating modes comprising a training mode and a classification mode.

3. The system as claimed in claim 1, wherein:
the image acquisition device acquires at least three images of the individual particle, wherein the individual particle is in-focus or out-of-focus,
the image processor creates the objects of the individual particle captured by the at least three acquired images, such that the stack of objects comprises at least one object wherein the individual particle is in-focus, and two objects wherein the individual particle is out-of-focus, and
the image processor further determines a set of values for the set of features of at least N features, wherein N is larger than or equal to 1, and wherein the determination of the set of values of the set of features involves data obtained from the at least one object wherein said particle is in-focus, and/or at least the two objects wherein the individual particle is out-of-focus.

4. The system as claimed in claim 1, wherein said translating arrangement is configured to move said sample device and said optical detection assembly relative to each other.

5. A method of creating objects of individual particles in a water sample held in a sample container, the method comprising:
translating an image acquisition area, formed by an image acquisition device and corresponding lens in the sample container, to multiple positions in the sample container, the image acquisition area being perpendicular to an optical axis of the lens;
acquiring images of the image acquisition area at the multiple positions in the sample container;
determining a set of features for an individual particle in the water sample captured by the acquired images by creating objects of the individual particle, wherein creating the objects of the individual particle comprises:
copying all pixels within an object periphery line surrounding the individual particle; and
subjecting said copied pixels to a filtration in at least one filter comprising a shape-filter, a size-filter, a contrast-filter or an intensity filter.

6. The method of claim 5, wherein said object periphery line surrounding the individual particle is shaped as a polygon or a circle.

7. The system as claimed in claim 1, wherein said image processor is programmed to identify complete stacks of objects, wherein said complete stacks of objects comprise at least one: (i) at least 5 objects, (ii) at least 9 objects, (iii) at least 15 objects, (iv) at least 25 objects, and (v) at least 49 objects.

8. The system as claimed in claim 1, wherein said image processor is programmed to determine values for a set of features comprising at least one of features relating to out-of-focus objects, features relating to grayscale versions of in-focus objects, features relating to thresholded versions of in-focus objects, and features relating to both in-focus and out-of-focus objects.

9. The system as claimed in claim 1, wherein the particle classification of particles is selected from a group consisting of bacteria, archaea, yeast, fungi, pollen, viruses, leukocytes, granulocytes, monocytes, Erythrocytes, Thrombocytes, oocytes, sperm, zygote, stem cells, somatic cells, crystals, fat droplets and mixtures thereof.

10. The system as claimed in claim 1, wherein the at least one image acquisition device is adapted to sequentially acquire sets of images and the artificial intelligent processor classifies particles captured by a first set of images and particles captured by at least a second set of images, creating a first ensemble of stacks of objects from said first set of images and a second ensemble of stacks of objects from said second set of images.

11. The system as claimed in claim 10, wherein said system is adapted to identify stacks of objects of said first ensemble of individual particles and stacks of objects of said second ensemble of said respective individual particles and detect changes between said stacks of objects of said first ensemble and stacks of objects of said second ensemble of said respective individual particles.

12. The system as claimed in claim 1, wherein said image processor is adapted to determine values for a set of features for unclassified particles, and to create an ensemble of sets of features, and wherein said unclassified particles are classified using said ensemble of sets of features.

13. A method of analyzing a test water sample held in a sample container for the presence of a target particle, the method comprising:
translating an image acquisition area, formed by an image acquisition device and corresponding lens in the sample container, to multiple positions in the sample container;
acquiring at least 3 images of individual particles, respectively, in said test water sample at multiple positions in the sample container, wherein said individual particles respectively are in-focus or out-of-focus;
creating objects of said individual particles, respectively, captured by said acquired images and providing stacks of objects for each individual particle;
identifying complete stacks of objects, each identified complete stack of objects at least comprising an object wherein the corresponding individual particle is in-focus and two objects wherein the corresponding individual particle is out-of-focus;
determining a set of features of at least N features for each of said identified complete stacks of objects, wherein N is larger than or equal to 1; and
associating said set of values for said determined set of features for each individual particle to classify said individual particle and to determine if at least one target particle has been classified from among the individual particles.

14. The method as claimed in claim 13 further comprising:
performing a quantitative analysis for determining the number of target particles in said test water sample.

15. The method as claimed in claim 13, further comprising providing the test water sample.

* * * * *